(12) United States Patent
Lecht et al.

(10) Patent No.: US 12,220,438 B2
(45) Date of Patent: Feb. 11, 2025

(54) PROTEIN BASED CANNABIS COMPOSITIONS

(71) Applicant: IZUN PHARMACEUTICALS CORP., New York, NY (US)

(72) Inventors: Shimon Lecht, Petah Tikva (IL); Olga Gabay, Jerusalem (IL); Adi Lahiani Hafzadi, Jerusalem (IL); William Z. Levine, Jerusalem (IL)

(73) Assignee: DAY THREE LABS MANUFACTURING INC., Denver, CO (US)

( * ) Notice: Subject to any disclaimer, the term of this patent is extended or adjusted under 35 U.S.C. 154(b) by 0 days.

(21) Appl. No.: 18/401,503

(22) Filed: Dec. 31, 2023

(65) Prior Publication Data

US 2024/0131099 A1    Apr. 25, 2024

Related U.S. Application Data

(63) Continuation of application No. 17/638,827, filed as application No. PCT/IL2020/050930 on Aug. 26, 2020, now abandoned.

(60) Provisional application No. 62/893,201, filed on Aug. 29, 2019.

(51) Int. Cl.
| | | |
|---|---|---|
| *A61K 36/185* | (2006.01) | |
| *A61K 31/05* | (2006.01) | |
| *A61K 31/352* | (2006.01) | |
| *A61K 38/01* | (2006.01) | |
| *A61K 47/36* | (2006.01) | |

(52) U.S. Cl.
CPC ............ *A61K 36/185* (2013.01); *A61K 31/05* (2013.01); *A61K 31/352* (2013.01); *A61K 38/011* (2013.01); *A61K 47/36* (2013.01); *A61K 2236/35* (2013.01)

(58) Field of Classification Search
None
See application file for complete search history.

(56) References Cited

U.S. PATENT DOCUMENTS

| | | |
|---|---|---|
| 2020/0170272 A1 | 6/2020 | Bromley |
| 2020/0254104 A1 | 8/2020 | Chancey |

FOREIGN PATENT DOCUMENTS

| | | |
|---|---|---|
| WO | 2018112479 | 6/2018 |
| WO | 2018191584 | 10/2018 |

OTHER PUBLICATIONS

Nikolaidis et al., "On the reversibility of ethanol-induced whey protein denaturation," Food Hydrocolloids. vol. 84, Nov. 2018, pp. 389-395 https://doi.org/10.1016/j.foodhyd.2018.05.051 (Abstract only).

*Primary Examiner* — Michael V Meller

(57) ABSTRACT

Described herein are novel compositions comprising a *Cannabis* component selected from the group consisting of: a cannabinoid, a flavonoid and a terpenoid; and a protein, selected from the group consisting of whey and a plant protein. According to an embodiment, the *Cannabis* component is non-covalently bound to the whey or to the plant protein. The plant protein may be selected from the group consisting of: soy protein, pea protein, rice protein, hemp protein, and hops protein or other plant derived protein.

11 Claims, 2 Drawing Sheets

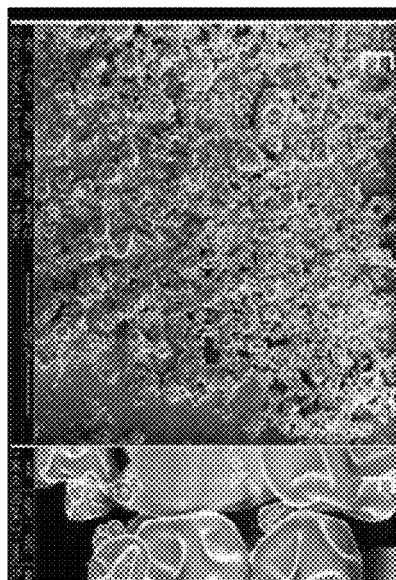
Fig. 1E
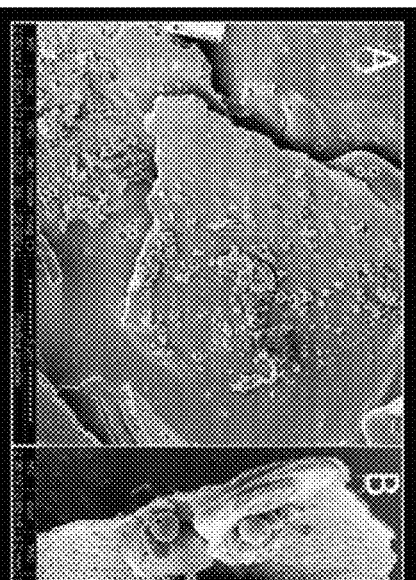
Fig. 1A
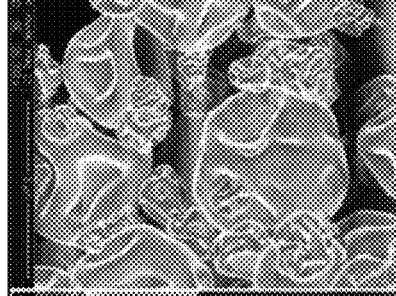
Fig. 1F
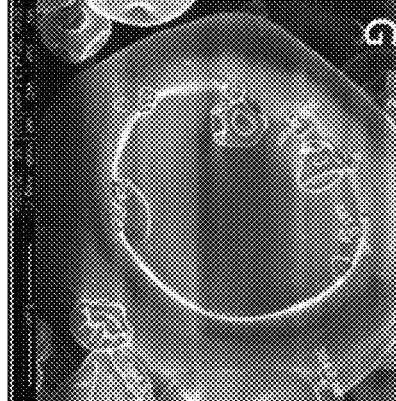
Fig. 1G
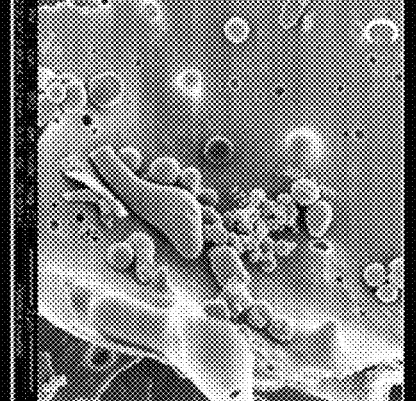
Fig. 1B
Fig. 1C
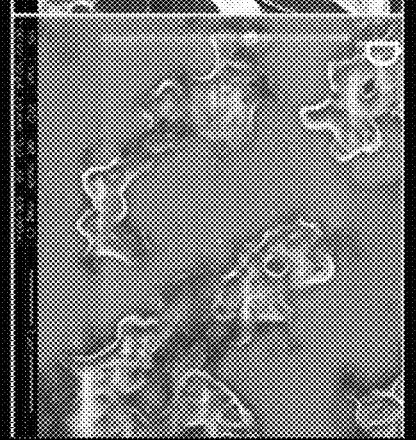
Fig. 1H
Fig. 1D

PROTEIN BASED CANNABIS COMPOSITIONS

CROSS REFERENCE TO RELATED APPLICATIONS

This is a continuation of U.S. patent application Ser. No. 17/638,827 filed on Feb. 27, 2022, which is the U.S. National Stage of International Patent Application No. PCT/IL2020/050930 filed on Aug. 26, 2020, which in turn claims the benefit of U.S. Provisional Patent Application 62/893,201, filed Aug. 29, 2019; the contents of which is incorporated by reference herein in its entirety.

FIELD

Provided herein are compositions comprising a *Cannabis* component, and a protein.

BACKGROUND

*Cannabis* is a genus of plants comprising the species *Cannabis sativa, C. indica,* and *C. ruderalis. Cannabis* plants have been cultivated for a variety of uses including making fibers (hemp), medicinal use and recreational drug use. *Cannabis* is also commonly known as marijuana.

One of the most common ways that *Cannabis* is used for medicinal use in many countries (also known as medical marijuana) is through smoking. Smoking *Cannabis* is typically performed by using a pipe, by using a water-pipe (also known as a bong) which filters the smoke through water before inhalation or by rolling in paper to form marijuana cigarettes, also known colloquially as "joints." The part of the plant typically used for smoking is the whole flower and budding leaf.

Cannabinoids are compounds active on cannabinoid receptors in humans. Cannabinoids of plant origin, also known as phyto-cannabinoids, are abundant in plants of the *Cannabis* genus. Two known cannabinoids which are present in relatively high concentrations in *Cannabis sativa* are tetrahydracannabinol-acid (THCA) or its decarboxylated product tetrahydracannabinol (THC) and cannabidiolic acid (CBDA) or its decarboxylated product cannabidiol (CBD). Psychoactive and other medical effects of many of the cannabinoids have been studied. For example, THC was found to have psychoactive (calming) effects, analgesic effects, antioxidant effects and to increase appetite. CBD was found to have neuroprotective effects and to have ameliorative effects in patients with schizophrenia and Parkinson's disease.

In addition to cannabinoids, terpenoids and flavonoids are present in *Cannabis* species. Some terpenoids were found to have biological effect and to contribute to a portion of the pharmacological effects of *Cannabis* plant matter. Exemplary terpenoids present in *Cannabis* plant matter include Beta-myrcene and alpha-pinene.

Although individual chemical components of *Cannabis* have been isolated, many jurisdictions approve the use and sale of medical *Cannabis* plant matter for a variety of indications. Research has shown that there are potential benefits to medical *Cannabis* including but not limited to: pain relief, such as chronic pain or cancer related pain, neuropathic pain; lack of appetite, and nausea such as in patients with HIV/AIDS and in patients receiving chemotherapy; autoimmune disease, such as multiple sclerosis; epilepsy; glaucoma; neurodegenerative disease and post-traumatic stress disorder (PTSD). Inflammatory disease, such as Crohn's disease is another indication in which *Cannabis* may have a positive effect.

Smoking medical *Cannabis*, although proven to be beneficial in certain indications, has disadvantages. Since *Cannabis* is a plant, amounts of active ingredients in the part of the plant being smoked may differ depending on the part of the plant and from plant to plant. Changing growing conditions (such as amount of light that a plant receives per day, or temperature) may vary at a *Cannabis* growing facility thereby providing product in which concentration of active ingredients vary over the course of the year. As a result, a patient treated using medical *Cannabis* may lack control over proper dosing of active cannabinoids.

Another disadvantage of smoking medical *Cannabis* is the negative impact of some of the constituents of *Cannabis* smoke. The smoke from the plant matter may comprise carcinogens in addition to the desired cannabinoids.

SUMMARY

Described herein are novel compositions comprising a *Cannabis* component selected from the group consisting of: a cannabinoid, a flavonoid and a terpenoid; and a protein, selected from the group consisting of whey and a plant protein. According to an embodiment, the *Cannabis* component is non-covalently bound to the whey or to the plant protein. The plant protein may be selected from the group consisting of: soy protein, pea protein, rice protein, hemp protein, and hops protein or other plant derived protein. Optionally, the composition may be dried. Optionally, the composition may comprise one *Cannabis* component, and may be free of other *Cannabis* components.

Compositions described herein are water-dispersible and have higher bioavailability, increased gastro-intestinal absorption, and/or extended half-life when compared to known compositions.

Additionally, described herein are methods for making compositions, comprising a *Cannabis* component/s selected from the group consisting of: a cannabinoid, a flavonoid and a terpenoid; and a protein, selected from the group consisting of whey and a plant protein. Edible, drinkable and otherwise food-like compositions are also described herein.

BRIEF DESCRIPTION OF THE DRAWINGS

FIGS. 1A-1H depict scanning electron photo micrographs. Lyophilized CBD-Whey products (FIG. 1A-FIG. 1C) and spray dried granules of the same product (FIG. 1E-FIG. 1G). The lyophilized product demonstrates a lattice-like structure of fused nanostructures, which is expected during this method of drying. The apparent deformation of granules in the spray-dried product is most probably due to the required aggressive drying during preparation for SEM analysis. FIG. 1D and FIG. 1H depict lyophilized and spray dried particles upon dispersal in water without shaking, respectively. In both panels (FIG. 1D and FIG. 1H) a submicron structure of the product are clearly visible;

DETAILED DESCRIPTION

I. Terms

Figure 2:
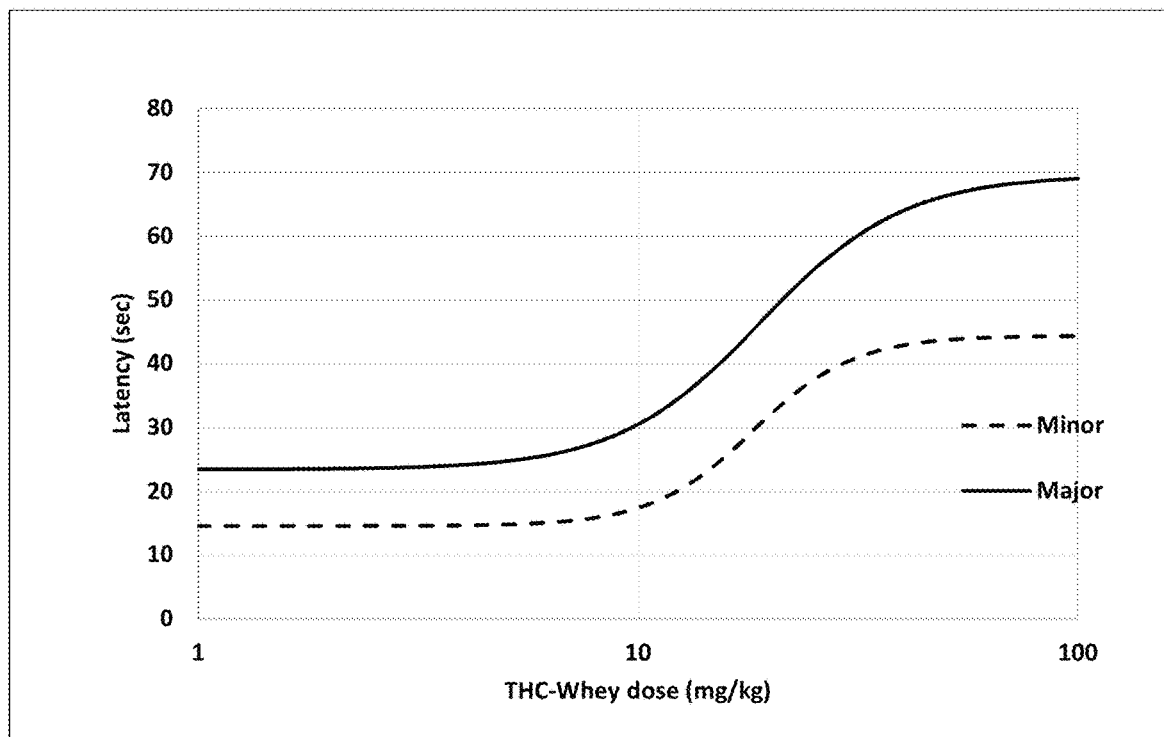
FIG. 2 depicts a dose response curve upon administration of THC-Whey to mice using a hot-plate pain model.

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides or peptides or proteins or portions or fractions thereof are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Cannabinoid: a compound having a cannabinoid structure. Preferably, a phytocannabinoid. A cannabinoid may be produced synthetically, for example, through a chemical synthetic process or by using a biological organism such as a yeast or a bacteria modified to produce the cannabinoid. Alternatively, a cannabinoid may originate from a *Cannabis* plant. A cannabinoid may be isolated, in pure form, or in combination with other cannabinoids. Optionally, a cannabinoid may be a decarboxylated cannabinoid or otherwise heat-transformed cannabinoid, or other cannabinoid having the structure of a metabolite which has underwent metabolic transformation in the human body. Optionally, the cannabinoid is a cannabimimetic.

*Cannabis*: a plant from the family Cannabaceae, optionally *Cannabis sativa, indica* and *ruderalis* and fiber-type hemp. Preferably a plant comprising a cannabinoid.

CBD: cannabidiol. A cannabinoid having the structure:

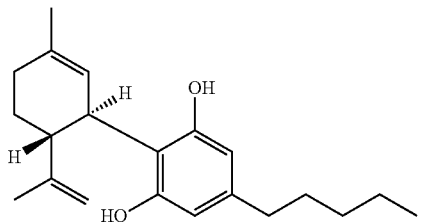 [SMILES: C=C(C)[C@@H]1CCC(C)=C[C@H]1c1c(O)cc(CCCCC)cc1O]

Flavonoid: A flavonoid is a polyphenolic compound, which can naturally occur, typically in plants. A flavonoid may be a flavan, isoflavonoid, flavanonol, flavanone, anthoxanthin, or anthocyanidin.

Terpene: A family of compounds characterized by the presence of the repeating carbon skeleton of isoprene. This family includes modification of terpenes that generate terpenoids and isoprenoids. Terpenes are a class of compounds found in many plants and are often the main fragrant component in plant-derived essential oils.

THC: tetrahydrocannabinol. A cannabinoid having the structure:

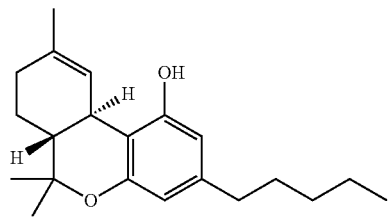 [SMILES: CCCCCc1cc(O)c2c(c1)OC(C)(C)[C@@H]1CCC(C)=C[C@@H]21]

II. Overview of Several Embodiments

Provided herein are compositions comprising a *Cannabis* component selected from the group consisting of: a cannabinoid, a flavonoid and a terpenoid and having enhanced physical and biological characteristics when compared to known compositions Preferably, the cannabinoid used is a phyto-cannabinoid. Preferably, it is a phyto-cannabinoid present in *Cannabis* plant. The cannabinoid may be extracted from a plant or synthetically produced. Preferably the cannabinoid is CBD or THC. The THC may be delta9-THC or delta8-THC.

Other cannabinoids which can be used in compositions described herein include but are not limited to one or a combination of: cannabigerol (CBG), cannabigerolic acid (CBGA), cannabigerol monomethyl ether (CB GM), cannabichromene (CBC), cannabichromanone (CBCN), cannabichromenic acid (CBCA), cannabivarichromene (CBCV), cannabichromevarinic acid (CBCVA), isotetrahydrocannabinol (iso-THC), cannabinol (CBN), cannabinolic acid (CBNA), cannabinol methyl ether (CBNM), cannabinol $C_4$ (CBN-$C_4$), cannabinol $C_2$ (CBN-$C_2$), cannabinol $C_1$ (CBN-$C_1$), cannabinodiol (CBND), cannabinovarinic acid (CBNVA), cannabinovarin (CBNV), cannabielsoin (CBE), cannabielsoic acid A (CBEA-A), Cannabielsoic acid B (CBEA-B), cannabicyclol (CBL), cannabicycloic acid (CBLA), cannabicyclovarin (CBLV), cannabitriol (CBT), cannabitriolvarin (CBTV), ethoxy-cannabitriolvarin (CBTVE), cannabivarin (CBV), cannabinodivarin (CBVD), tetrahydrocannabivarin (THCV), cannabidivarin (CBDV), cannabigerovarin (CB GV), cannabigerovarinic acid (CBGVA), cannabifuran (CBF), dehydrocannabifuran (DCBF), cannabirispol (CBR).

According to an embodiment, the composition comprises a terpenoid. The terpenoid is selected from the group consisting of: bisabolol, caryophyllene, borneol, terpinolene, terpineol, pinene, phytol, phellandrene, nerolidol, myrcene, menthol, linalool, limonene, isopulegol, humulene, guaiol, geranyl acetate, geraniol, eucalyptol (Cineol), cymene, delta 3 Carene, camphor, camphene, valencene, and ocimene.

Methods for Manufacture:

An aqueous fraction containing plant protein/s is prepared as follows: The plant-derived material is macerated and then the water-soluble fraction is extracted by adding water in the presence or absence of mixing. Thereafter, the water mixture is filtered (optionally 1 micrometer to 1 mm) and the filtrate is subjected to additional sedimentation. The sedimentation can be passive or forced via centrifugal force. In another embodiment the water-dispersed and/or dissolved proteins undergo fractionation according to their molecular weight via dialysis, size exclusion, ultracentrifugation or other methods. Upon collection of the desired protein fraction, the *Cannabis* component such as cannabinoid is dissolved in an organic solvent, and the organic phase is added to the protein fraction solutions. Complexes between *Cannabis* component and the proteins are formed via nanoprecipitation or emulsification or other methods. The residual organic phase is removed via dialysis, diafiltration, rotary evaporation, lyophilization, spray drying or other methods resulting with protein-based solid core particles.

Physical Characteristics:

According to an embodiment, the compositions comprising a *Cannabis* component and whey or a plant protein are in the form of an aqueous suspension. It has been found that compositions form stable aqueous suspensions in which the *Cannabis* component remains suspended at about 2 mg/ml, even after centrifugation of the aqueous suspension at 3,300 RPM for one minute. In contrast, known compositions in which there was no encapsulation or other form of physical interaction between the *Cannabis* component and the whey or plant protein, centrifugation of the aqueous suspensions at 3,300 RPM for one minute caused the *Cannabis* component, such as a cannabinoid, to sediment out of aqueous phase.

*Cannabis* compositions according to an embodiment, can be prepared having the ratios described in Table 1 below.

TABLE 1

| Cannabis component amount (mg) | Amount of protein (mg) |
|---|---|
| 0.008 | 1 |
| 0.01 | 1 |
| 0.025 | 1 |
| 0.05 | 1 |
| 0.1 | 1 |
| 0.18 | 1 |
| 0.25 | 1 |
| 0.4 | 1 |
| 0.5 | 1 |
| 0.7 | 1 |
| 0.8 | 1 |
| 0.9 | 1 |
| 1 | 1 |
| 1.2 | 1 |

Optionally, the ratio of *Cannabis* component to protein, by weight, is between 0.008 to 1 and 1.2 to 1. Preferably, the ratio of *Cannabis* component to protein, by weight, is between 0.025 to 1 and 0.5 to 1.

Optionally, the protein fraction used in compositions described herein is a water-suspended fraction of the protein. The protein may have a molecular weight of between 1 and 100 kilodalton (kDa), preferably between 2 and 10 kDa or 10 and 80 kDa or most preferably between 20 and 70 kDa or 30 and 67 kDa.

Advantages of Compositions Described Herein:

The following advantages were found for novel compositions described herein: enhanced pharmacokinetic profile in terms of increased bioavailability, increased $C_{max}$, shorter $t_{max}$, higher AUC, more uniform and easier dispersion in an aqueous carrier, as well as taste masking characteristics of the composition.

Edible Compositions:

Some embodiments relate to edible compositions comprising a *Cannabis* component selected from the group consisting of: a cannabinoid, a flavonoid and a terpene; and a protein, selected from the group consisting of whey and a plant protein. The edible composition may be in the form of a candy such as a chocolate, cookie, a composition for sprinkling on food, a popsicle, a protein shake powder and a beverage, for example, a beer, a soft drink, mineral water and a milkshake. The beverage can be carbonated or non-carbonated, and the beverage can be a juice from natural source, concentrate or artificial.

Methods for Treatment:

Some embodiments relate to methods for treating a disease comprising administering to a patient in need thereof, a therapeutically effective amount of a composition comprising a protein and a *Cannabis* component selected from the group consisting of: a cannabinoid, a flavonoid and a terpenoid described herein. The therapeutically effective amount may be an amount, which upon administration to a patient, ameliorates a symptom associated with the disease or modifies the level of a biological marker associated with the disease in the patient.

According to an embodiment, the method of treatment comprises treating a patient in need thereof with a cannabinoid, optionally, THC or CBD. The amount of THC is optionally between 0.1 and 25 mg per dose, 1 to 10 mg per dose, or 1 to 5 mg per dose. The amount of CBD is optionally between 0.1-200 mg/dose, 1-10 mg per dose, 10-25 mg per dose, 15-50 mg per dose, or 100-200 mg per dose. A dose may be administered once daily, twice daily, three times a day, or four times a day. Alternatively, the dose may be administered between 1 and 3 times a week.

According to an embodiment, the method for administration is through an oral route (per-os). Optionally, the route of administration is intranasal, mucosal, sublingual, dermal, or buccal. Optionally, the route is parenteral injection, via intravenous, subcutaneous, or intramuscular routes.

The following examples are provided to illustrate certain particular features and/or embodiments. These examples should not be construed to limit the disclosure to the particular features or embodiments described.

EXAMPLES

Example 1: Manufacture of Compositions Comprising Whey and *Cannabis* Component

Whey protein powder (about 20 g) was dissolved in about 100 ml water, centrifuged for 5 min at 3,300 RPM and supernatant was diafiltrated to about 40 ml. For manufacturing the composition, 1 g of concentrated whey protein was diluted to 100 ml and supplemented with 25 ml of phytocannabinoid and terpenes solution at a concentration of 1.6 mg/ml total cannabinoids and terpenes. Thereafter, the mixture was left for about 2 h incubation at room temperature followed by diafiltrating using a 10 kDa cutoff membrane. The final volume was reduced to about 40 ml and used for downstream applications or dried via freeze-drying or spray-drying to achieve a solid powder form.

Example 2: Manufacture of Compositions Comprising Plant-Based Proteins and *Cannabis* Component Plant biomass comprising plant protein (about 30 g of plant biomass) was ground to about 5 mm grain size. The ground biomass was then transferred into a beaker and about 200 ml of water were added. The mixture was stirred for at least 2 h using a propeller mixer at maximum speed around 1,000 RPM. Thereafter, the mixture was left to settle for about 1 h or filtered through Whatmann paper No. 1 and subjected to centrifugation for 5 min at 3,300 RPM and supernatant was diafiltrated to about 40 ml. The *Cannabis* component was added and the composition was then further processed in a similar fashion as in example 1.

The starting material for this procedure may comprise soy protein powder, pea protein powder, hops granules, or hemp protein powder.

Example 3A: Dispersion of Compositions

Composition 1, as prepared in example 1 was either spray dried or lyophilized. To compare the solubility properties of Composition 1 obtained through spray drying and lyophilization, equal amount of powders were dispersed in 20 ml glass bottles containing an equal amount of water. The time until complete dispersion as evaluated by visual observation was measured.

The results indicate that whereas lyophilized Composition 1 powder was completely dispersed after 2 minutes without the need for a shake, spray-dried Composition 1 powder dispersion was slightly slower and was completed at 3 min post initiation with application of mild mechanical shaking. In both instances, an opaque, uniform suspension indicated dispersion. The slightly faster dispersion of the lyophilized composition 1 than spray-dried, may be attributed to the high volume of the dry structure providing larger surface area for material-water contact.

Example 3B: Testing of Particle Size of Compositions

Particle size distribution and morphology were obtained using a scanning electron microscope (SEM) dynamic light scattering (DLS) techniques. For SEM, powders were tested in their solid form and after they were dispersed in water immediately prior to imaging. For DLS, a Zetasizer nano ZDP was used to measure the size of dispersed particles in water. The data presented as a Z-average of triplicates, is the intensity weighted mean hydrodynamic size of the ensemble collection of particles measured by DLS. PDI is a representation of the distribution of size populations within a given sample. The numerical value of PDI ranges from 0.0 (for a perfectly uniform sample with respect to the particle size) to 1.0 (for a highly polydisperse sample with multiple particle size populations). PDI less than 0.4 was considered as acceptable for uniformity of distribution.

To obtain information about the surface topography of two types of CBD-Whey powders, spray dried and lyophilized, SEM analysis was performed. The powders in their solid form demonstrated significant differences in their topography. The lyophilized product appeared to be present in a continuous sheet of material with bean-like micron-sized granules (FIG. 1A-C). The powder that was prepared through spray drying appeared to be in aggregates of micron-sized granules (FIG. 1E-G). The apparent deformation of granules in the spray-dried product is most probably due to the required aggressive drying during preparation for SEM analysis. Upon dispersion in water, both products demonstrate clusters of several sub-micron particles, suggesting that drying method has no negative effect on the sub-micron particles of Composition 1 (FIGS. 1D and H).

In order to measure the effect of drying technique on the size of particles, the powders from different preparations were dispersed in 1.5 ml water and 1 ml of each sample was transferred to cuvettes. Each cuvette examined in zetasizer in triplicates. The particle size of Composition 1 prepared in two different ways was essentially the same (344 nm for spray-drier and 355 nm for the lyophilizer). In addition, the PDI was 0.24 and 0.28 respectively, which are both below 0.3, indicating a uniformity of size distributions. In conclusion, spray dried composition 1 is advantageous in that it has more uniform granules as compared to lyophilized composition 1 and can form flowing powder, whereas lyophilized composition 1 disperses slightly faster than spray-dried composition.

Example 3C: Testing of Physical Characteristics of Compositions

Composition 1, as prepared in example 1, comprising whey and CBD, was tested for solubility in comparison to a standard, off the shelf product, comprising whey and CBD. In addition, whey-only powder was used as a negative control.

The following procedure was performed to composition 1 and to the commercially available product, CBD recovery protein, made by Floyd's of Leadville, Leadville, Colorado, USA, hereinafter, "Floyd's". This composition was used as a standard off-the shelf whey/CBD product, representative of currently available products.

To test Floyd's and the association between the whey and the CBD in Floyd's, 2 g of Floyd's were added to 50 ml water and gently but thoroughly mixed by inverting upside-down, and then dialyzed against a 10 kDa cutoff membrane. The dialyzed product was then spun in a centrifuge for 1 min at 3,300 RPM. The amount of CBD in the aqueous supernatant was reduced to undetectable values, indicating that the CBD is not present in the aqueous phase and is most probably was removed during dialysis.

Next, 2.4 mg of pure CBD was added to the "Floyd's" product and the aforementioned procedure of mixing and dialysis was repeated. The results were similar as before, and no CBD was detected.

To verify these results, a mixture of 2.9 mg of CBD and 0.5 g of whey powder was prepared and 1 ml of water were added. The same protocol of dialysis and centrifugation was performed, and the results showed that the CBD did not remain in the supernatant.

Composition 1 was added to 1 ml water and mixed gently but thoroughly by inverting upside-down. The composition was then spun for 1 min at 3,300 RPM, and the supernatant was tested for presence of CBD resulting with 191 μg/ml of CBD in the supernatant.

Then 1.9 mg of pure CBD (not protein-associated) was added to the composition and then the composition was spun at the same conditions. The external addition of CBD was completely removed after spinning, returning to the original concentrations (191 μg/ml) of CBD based on the Composition 1.

These results suggest that composition 1 is a composition in which CBD and whey protein are associated, allowing for formation of stable suspensions. In addition, commercially available compositions comprising whey and CBD appear to contain CBD and whey, but they are the result of mixing whey powder with solid CBD powder (crystals, isolate) without any physical association to each other, other than present in the same vessel/container, resulting in water-insoluble solid CBD to rapidly precipitate out of suspension.

Example 4: Testing of Biological Characteristics of Compositions Comprising THC

A study was performed to test the pharmacokinetic profile of THC, in various forms, in male Sprague-Dawley rats, aged between 9-11 weeks. Rats weighing 280-310 g at study initiation were acclimated for 7 days and then administered a test drug. 72 rats were divided into 6 groups of 12 rats in each group. The groups were administered a single dose of the test drugs according to the following grouping:

Group A: THC in sesame oil, per os. Volume: 2 ml/kg. Dose of 15 mg/kg.

Group B: THC-albumin composition, per os. Volume: 2 ml/kg. Dose of 15 mg/kg. This composition was prepared using the procedure described in US Patent Application Publication 2015/0265720. Briefly, THC was dissolved in ethanol and added to protein solution at 30% ethanol, followed by incubation for 24 hours at 37° C.

Group C: THC-whey protein composition, per os, prepared as described in Example 1. Volume: 2 ml/kg. Dose of 15 mg/kg.

Group D: THC, intravenously (IV), dissolved in ethanol:Cremophor:Saline (1:1:18). Volume: 2 ml/kg. Dose of 5 mg/kg.

Group E: THC-albumin composition, subcutaneous. Volume: 2 ml/kg. Dose of 11.6 mg/kg. This composition was prepared using the procedure described in US Patent Application Publication 2015/0265720.

Group F: THC-whey protein composition, sublingual. Volume: 0.2 ml/kg. Dose of 7.7 mg/kg.

THC-albumin and THC whey protein compositions were dissolved in saline. The Group F sublingual administration was dissolved in a small amount of saline to form a paste-like composition.

Rats were observed following dosing for signs of behavioral changes, reaction to test article or illness. No abnormalities were observed.

The test items were administered and blood samples were collected from the retro-orbital sinus at 0.25, 0.5, 1, 2, 4, 5, 6, 8 and 24 hours post administration. Plasma was collected and stored at −80° C. Control plasma samples were collected from 3 naïve rats. Plasma concentrations were determined for THC, THC-COOH (11-nor-9-carboxy-THC) and THC-OH (11-hydroxy-THC).

The pharmacokinetic parameters of THC in the various groups were tabulated and appear in table 2 below.

idly absorbed, with maximum concentrations attained within 2 hours after dosing. The terminal $t_{1/2}$ ranged from about 2 hours after sublingual administration to 16 hours after per os administration. Oral delivery of THC in sesame oil formulation resulted in bioavailability higher than expected for THC most probably due to lymphatic absorption of high dose sesame oil-containing formulations. Interestingly, the absolute bioavailability after subcutaneous and sublingual administration was higher than IV.

Example 5: Testing of Pharmacokinetic Parameters of Compositions Comprising CBD

A study was performed to test the pharmacokinetic profile of CBD, in various forms, in male Sprague-Dawley rats, aged 8 weeks at study initiation. Rats weighing 190-240 g at study initiation were acclimated for at least 5 days, then deprived of food for at least 4 hours and then administered a test drug. 36 rats were divided into 3 groups of 12 rats in each group. The groups were administered a single dose of the test drug according to the following grouping:

Group A: CBD-whey protein composition, per os, prepared as described in Example 1. Volume: 10 ml/kg. Dose of 21 mg/kg.

Group B: Floyd's CBD Recovery Whey Protein product, described above, per os. Volume: 10 ml/kg. Dose of 21 mg/kg.

Group C: CBD in olive oil, per os. Volume: 10 ml/kg. Dose of 21 mg/kg.

Compositions for groups A and B were dissolved in saline.

The test items were administered and blood samples were collected from the retro-orbital sinus at 0.25, 0.5, 1, 2, 3, 4, 6 and 8 hours post administration. Plasma was collected and stored at −80° C. Control samples were from blood drawn from 3 naïve rats. Plasma concentrations were determined for CBD. The pharmacokinetic data is shown in Table 3.

TABLE 2

| | Group | | | | | |
|---|---|---|---|---|---|---|
| | A | B | C | D | E | F |
| | | | Formulation | | | |
| Parameter | Sesame oil | Albumin | Whey | IV | Albumin | Whey |
| Dose (mg/kg) | 15 | 15.1 | 15 | 5 | 11.6 | 7.73 |
| $t_{1/2}$ (h) | 4.38 | 16.3 | 4.24 | 10.8 | 7.93 | 2.13 |
| $t_{max}$ (h) | 2 | 0.25 | 0.5 | 0.0833 | 2 | 1 |
| $C_{max}$ (ng/mL) | 74.6 | 104 | 108 | 1008 | 152 | 1284 |
| $C_{max}/D^*$ (kg*ng/mL/mg) | 4.98 | 6.92 | 7.16 | 202 | 13.1 | 166 |
| $AUC_{0-t}$ (h*ng/mL) | 923 | 686 | 375 | 575 | 1797 | 2144 |
| $AUC_{0-\infty}$ (h*ng/mL) | 946 | 988 | 384 | 607 | 2070 | 2145 |
| $AUC_{0-\infty}/D^\$$ (h*kg*ng/mL/mg) | 63.0 | 65.4 | 25.5 | 121 | 178 | 277 |
| $V_z/F$ (mL/kg) | 100288 | 359289 | 239959 | 128472 | 64321 | 11100 |
| CL/F (mL/h/kg) | 15862 | 15285 | 39198 | 8233 | 5620 | 3604 |
| F (%) | 52 | 54 | 21 | 100 | 147 | 228 |

Conclusions: After IV administration, maximum plasma concentrations were attained immediately after dosing and declined thereafter with a terminal $t_{1/2}$ of about 10 hours in an analysis that included the 24 hr time point. The CL (8233 mL/h/kg) exceeded the plasma flow to the liver, suggesting that THC is a high extraction ratio compound. Also, the Vz exceeded the total body water, indicating tissue distribution. After extravascular administration, THC was generally rap-

TABLE 3

| Parameter | Unit | A-CBD and whey | B-Floyd | C-CBD olive oil |
|---|---|---|---|---|
| $t_{1/2}$ | h | 24.5 | 3.2 | 5.9 |
| $T_{max}$ | h | 0.5-1 | 1 and 3 | 3-4 |
| $C_{max}$ (average) | ng/ml | 405 | 52 | 112 |

TABLE 3-continued

| Parameter | Unit | A-CBD and whey | B-Floyd | C-CBD olive oil |
|---|---|---|---|---|
| $AUC_{0-t}$ | ng/ml*h | 1188 | 268 | 533 |
| AUC 0-inf_obs | ng/ml*h | 3487 | 342 | 1140 |
| Relative $C_{max}$ | | 779% | 100% | 215% |
| Relative bioavailability | | | | |
| 0-t | | 444% | 100% | 199% |
| 0-inf | | 1019% | 100% | 333% |

As can be seen in Table 3, the Cmax and pharmacokinetic profile in general is improved when CBD is administered to group A using compositions prepared according to example 1, when compared to other compositions.

Example 6: Manufacture of Edible Compositions Comprising Cannabinoids

Gummy candies, also known as gummies or "gummy-bears", were made from CBD-Whey and THC-Whey compositions prepared as described in Example 1. Two technologies were employed to successfully make gummies gelatin-based gummies and pectin-based gummies Agar agar-based gummies were also attempted but they did not obtain a successful gummy-like texture.

Gelatin-based gummies were prepared as follows: 180 mg of either CBD-Whey or THC-Whey prepared as disclosed in example 1 were dissolved in 115 ml of water, mixed with 12 g of gelatin and left at room temperature for 25 minutes. The solution was flash warmed for 3-5 minutes, until bubbles were observed, and transferred to molds. The samples were placed at 4° C. for 16 hours to solidify. Gummies having 5 or 10 mg of cannabinoid per unit were prepared.

Pectin-based gummies were prepared as follows: 180 mg of CBD-Whey was dissolved in 115 ml water and was flash warmed for 3-5 minutes (until the first bubbles were observed) and pectin/sugar mix added (3 g:15 g). After all the pectin and sugar completely dissolved, 1 ml of lemon juice was added to the mixture. Following mixing by hand for 5 secs, the solution was transferred to a mold and left at room temperature for 16 hours to solidify. Each gummy was prepared to have 10 mg of CBD.

In conclusion, protein-cannabinoid compositions can be incorporated into edibles, for example gummies, to provide dosage forms having stability. Gelatin and pectin are suitable matrices to provide stable compositions.

Example 7: Blinded Tasting of Edible Compositions Comprising Cannabinoids

CBD-Whey was prepared as described in Example 1. As a control, whey without CBD (known herein as "Whey only") was used. "Whey only" powder was prepared following the same procedure as for CBD-Whey with omitting addition of CBD. The incubation step was performed with ethanol without any dissolved cannabinoid.

Samples of still water (Mei Eden bottled water), carbonated water (made by Tempo Soda), alcoholic lager beer (Carlsberg) and orange juice (made by Primor) were prepared using each of CBD-Whey and Whey only. 25 ml of beverage was prepared for each sample, and 45 mg of CBD-Whey (which contains 2.7 mg of CBD). CBD only samples in beverages were prepared by attempting to dissolve pure CBD (2.7 mg in 25 ml) in the beverages but crystalline CBD was visible, thereby rendering blinding impossible. The study continued with comparison of CBD-Whey and Whey only. Volunteers, who were *Cannabis* naïve, were given 8 samples, in a randomized order and were asked to fill a questionnaire relating to appearance, taste and smell of samples. Evaluations were performed by 6 volunteers for each of the 8 samples (four beverages with CBD-Whey and four beverages with Whey only.)

All participants indicated that Whey only as well as CBD-Whey were not transparent in all beverages that were evaluated. One participant indicated CBD-Whey was more transparent in orange juice than others. More than 50% of participants found CBD-Whey as visually appealing, with the exception of still water that received 35% positive reports. In the cases of carbonated water, beer and orange juice, the visual appearance was more appealing for CBD-Whey than Whey-only.

Upon olfactory examination, for all CBD-Whey containing beverages between 80% to 100% of participants reported positive experience. Only in the cases of still and carbonated water a negative experience was reported. However, the associated smell most probably is due to whey rather than CBD since whey-only samples received either same or higher negative percentage than CBD-containing beverages.

The CBD-associated bitter taste was partially masked, in particular in beverages with inherent flavor such as beer and orange juice. Surprisingly, some participants reported bitter taste in whey-only beverages. Based on these results, compositions according to example 1 successfully masked the taste of CBD.

Participants reported overall positive impression of the CBD-Whey that were dissolved in liquids with inherent flavor such as orange juice and beer. Though, water, either still or carbonated, received negative scores, it may be the result of whey itself rather than the presence of CBD in the liquid. Cumulatively, this study points towards compositions described herein as a viable nano-delivery system for dispersion in a variety of beverages that will provide a platform for solubilization and taste masking.

Example 8: THC-Whey Anti-Nociceptive Effect in Animal Models

An animal model was performed with THC-Whey prepared in accordance with Example 1. THC (without whey) was tested in equivalent doses via oral administration and compared to orally administered THC-Whey prepared according to Example 1 in a mouse model of acute pain based on the hot plate model.

Mice, of the C57BL/6JOlaHsd strain, weighing on average 23 g were 7 weeks old upon study initiation.

THC was dissolved in ethanol. The ethanolic solution was combined with food grade olive oil by mixing and prepared to appropriate concentrations for per-os administration. THC-Whey was lyophilized and reconstituted with saline for administration per-os. Oral administration to mice was performed using gavage needle. Mice were weighed at study initiation and fed ad libitum and housed in standard laboratory conditions with a 12 hour light and 12 hour dark cycle.

One day prior to the experiment, all mice were trained for the hot plate test for baseline reference value as and the following day, test items were administered. The hot plate evaluations began 30 minutes post administration. Each animal was placed on a hotplate 30 minutes post administration and latency, in seconds, was measured from placement on the hotplate until a showing of minor and major discomfort.

Minor discomfort was characterized by licking fore paws. And major discomfort was characterized by shaking rear paws. Observations were performed at 30 minute intervals until 240 minutes from administration. Each in vivo experiment was performed in two phases: the same mouse had participated in phase 1 and 2 for different test items. At least 1 week lapsed between the end of the first phase and the beginning of the second phase.

Six animals were administered, each of the test items in a volume of 10 ml per kg. The THC in olive oil test item was administered at doses of 10, 15, 20, 25, 30, and 35 mg per kg. The THC-Whey test item was administered at doses of 5, 10, 15, 20, 25, and 30 mg per kg. Statistical analysis was performed. Extreme outliers were identified using interquartile range. Values that were found to be above the upper fence (Q3+1.5*IQR) or below the lower fence (Q1−1.5*IQR) were considered as extreme outliers and omitted from calculations. No deviations from the protocol occurred.

Dose response curves were analyzed using sigma plot software and the R, $R^2$, min, max, $EC_{50}$ and hillslope parameters were calculated and determined for each time point for minor and major discomforts using all tested doses. THC in olive oil minor dose response parameters at each parameters are shown in Table 4:

| Time (min) | R | $R^2$ | min | Max | $EC_{50}$ | Hillslope |
|---|---|---|---|---|---|---|
| 30 | 0.6240 | 0.3894 | 11 | 19 | 29.8 | −22.110 |
| 60 | 0.5333 | 0.2844 | 14 | 22 | 21.0 | −125.957 |
| 90 | 0.3941 | 0.1553 | 15 | 23 | 24.2 | −98.896 |
| 120 | 0.3753 | 0.1408 | −3472771 | 20 | 45.5 | 48.598 |
| 150 | 0.3197 | 0.1022 | 15 | 23 | 15.9 | −63.278 |
| 180 | 0.5039 | 0.2539 | 15 | 22 | 17.3 | 203.360 |

THC in olive oil major dose response parameters at each parameters are shown in Table 5:

| Time (min) | R | $R^2$ | min | Max | $EC_{50}$ | Hillslope |
|---|---|---|---|---|---|---|
| 30 | 0.3627 | 0.1316 | 23 | 29 | 18.3 | −236.932 |
| 60 | 0.4082 | 0.1666 | 23 | 34 | 19.7 | −85.930 |
| 90 | 0.4014 | 0.1612 | 26 | 34 | −17.4 | −147.549 |
| 120 | 0.4157 | 0.1728 | 23 | 29 | 22.1 | −501.477 |
| 150 | 0.3711 | 0.1377 | 27 | 37 | 19.8 | −88.965 |
| 180 | 0.4289 | 0.1839 | 27 | 42 | 15.0 | −160.406 |

A sigmoid dose response curve for both major and minor discomfort post per os administration of THC in olive oil was impossible to generate.

THC-Whey minor dose response parameters at each parameter are shown in Table 6:

| Time (min) | R | $R^2$ | min | Max | $EC_{50}$ | Hillslope |
|---|---|---|---|---|---|---|
| 30 | 0.7261 | 0.5272 | 18 | 31 | 12.1 | −155.2993 |
| 60 | 0.9692 | 0.9393 | 16 | 44 | 13.7 | −4.6552 |
| 90 | 0.9478 | 0.8983 | 15 | 44 | 18.3 | −3.7382 |
| 120 | 0.9703 | 0.9415 | 13 | 44 | −21.7 | −1366.0978 |
| 150 | 0.982 | 0.9643 | 18 | 38 | 21.2 | −23.4176 |

THC-Whey major dose response parameters at each parameter are shown in Table 7:

| Time (min) | R | $R^2$ | min | Max | $EC_{50}$ | Hillslope |
|---|---|---|---|---|---|---|
| 30 | 0.8272 | 0.6843 | 21 | 58 | 30.7 | −110.3000 |
| 60 | 0.9298 | 0.8646 | 23 | 70 | 19.0 | −2.6620 |
| 90 | 0.9354 | 0.8749 | 25 | 278 | 64.5 | −2.6066 |
| 120 | 0.9377 | 0.8793 | 24 | 60 | 24.8 | −98.3770 |
| 150 | 0.9909 | 0.982 | 28 | 60 | 20.9 | −47.9617 |

Taking in consideration all of the above parameters, a dose response curve for minor discomfort at 90 min time and for major discomfort at 60 min time point post p.o. administration of THC-Whey was generated. The dose-response analysis led to calculation of minor $EC_{50}$=18.3 mg/kg and major $EC_{50}$=19.0 mg/kg, and can be seen in FIG. 2.

Figure 3:
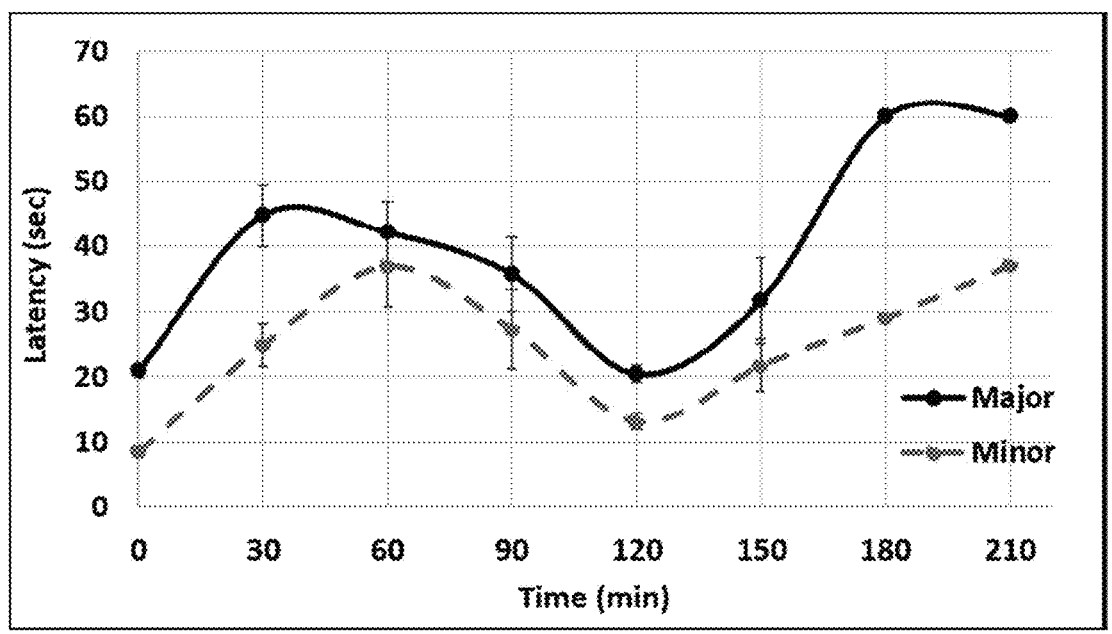
FIG. 3 depicts latency time to respond to hot-painful stimuli, an indicator of anti-nociceptive effect, in mice using a hot-plate model as a function of time after administration of a 20.0 mg/kg THC-Whey.

When THC-Whey was administered at 20.0 mg/kg, the dose closest to the $EC_{50}$, the latency over time was shown to have a biphasic time dependent response as shown in FIG. 3.

The hotplate mouse mode is an indicative in vivo assay for evaluating anti-nociceptive effects of novel compounds and formulations. In the hot-plate model the latency time to demonstrate painful discomfort is inversely correlated with the pain reducing effects of drugs, namely longer time to respond to the painful stimuli is indicative of stronger pain-relieving effect of a drug. Moreover, in hot-plate assay two readouts are recorded for the minor and followed by major discomfort sensation. It can be further extrapolated that minor and major discomfort have a translational relevance for human subjects. Superior pharmacodynamics effects for THC-Whey as compared with THC dissolved in oil have been demonstrated. THC-Whey was both more effective in reducing painful stimuli but also generated a longer lasting effect. It was not possible to generate a dose-response curve for the THC in olive oil formulation upon per os administration supporting the notion that THC exhibits a U-shape response, which poses difficulties in predicting the therapeutic dose. Furthermore, the variable pharmacodynamic effect of THC alone is supportive of the human based studies that report a highly variable effect of THC in oil-based formulations. In summary, THC-Whey induced a significant positive anti-nociceptive effect as early as 30 min post administration. The THC-whey composition results in a predictable dose-response behavior unlike THC in oil. Both oil and CannTrap-based formulations of THC demonstrated a biphasic time dependent response but with higher antinociceptive effect in the case of the Whey-based composition.

Example 9: Preparation of Whey-Terpene Composition

A Whey-Terpene composition was prepared as in example 1, but cannabinoids were not used, and in its place 1 ml of terpene solution was dissolved in ethanol and then incubated with the protein.

The terpene solution was called "Grand Daddy Purple" and is based on a *Cannabis* strain having the same name. The solution had the following profile:

| Terpene | Percent, by weight |
|---|---|
| β-Caryophyllene | 9.0 |
| D-Limonene | 7.6 |
| α-Humulene | 3.5 |
| Linalool | 5.1 |

-continued

| Terpene | Percent, by weight |
|---|---|
| β-Myrcene | 24 |
| α-Pinene | 50 |

The freeze-dried whey-terpene powder had a faint smell, but upon dispersing in water at as little as 1 mg powder in 50 ml of water, the terpene smell was noticeably present.

The whey-terpene powder retains smell for more than a year upon reconstitution (addition to water), whereas terpenes, without whey are volatile compounds which do not retain their smell for long.

Some embodiments described herein relate to: a composition comprising a Cannabis component selected from the group consisting of: a cannabinoid, a flavonoid and a terpene; and a protein, selected from the group consisting of whey and a plant protein, wherein the Cannabis component is non-covalently bound to the protein. Optionally, the Cannabis component is a cannabinoid, optionally, THC or CBD. Optionally, the protein is whey proteins. Optionally, the protein is a plant protein. Optionally, the plant protein is selected from the group consisting of: soy proteins, pea proteins, rice proteins, hemp proteins, and hops proteins. Optionally, the ratio of Cannabis component to protein, by weight, is between 0.008 to 1 and 1.2 to 1. Optionally, the ratio of Cannabis component to protein, by weight, is between 0.025 to 1 and 0.5 to 1. Optionally, the protein comprises a water-suspended fraction of the protein. Optionally, the protein has an average molecular weight of between 1 and 100 kilodalton (kDa). Optionally, the protein has an average molecular weight of between 30-67 kDa. Optionally, when the composition is in aqueous form at a cannabinoid concentration of 2 mg/ml and undergoes centrifugation at 3,300 RPM for 1 minute, the Cannabis component remains suspended. Optionally, the composition is in the form of an edible composition. Optionally, the composition is in the form of a candy, a chocolate, cookies, a sauce, a composition for sprinkling on food, a popsicle, a protein shake powder a beverage, a beer, a soft drink, alcoholic beverage, juice, gummy and a milkshake. Optionally, the composition is in a dry solid form. Optionally, the composition further comprises gelatin or pectin or agar-agar. Optionally, the Cannabis component is a terpene. Optionally, the Cannabis component is a cannabinoid, in the form of Cannabis extract. Optionally, the composition further comprises at least one terpene.

Some embodiments described herein relate to a method for treatment of a disease comprising administering to a patient in need thereof a composition comprising a Cannabis component selected from the group consisting of: a cannabinoid, a flavonoid and a terpene; and a protein, selected from the group consisting of whey and a plant protein, wherein the Cannabis component is non-covalently bound to the protein. Optionally, the disease is selected from the group consisting of pain, chronic pain, cancer related pain, neuropathic pain; lack of appetite, nausea, autoimmune disease, multiple sclerosis, epilepsy, glaucoma, neurodegenerative disease, post-traumatic stress disorder (PTSD), inflammatory disease and Crohn's disease. Optionally, the composition is administered through the oral route. Optionally, the disease is selected from the group consisting of: inflammatory conditions secondary to a disease; cytokine storm and insomnia.

Some embodiments described herein relate to a method for manufacture of a composition comprising: dissolving a Cannabis component in an organic solvent to form an organic solution; and combining the organic with an aqueous protein solution to form a crude Cannabis-protein complex. Optionally, the method further comprises forming a complex between the Cannabis component and the protein using nanoprecipitation or emulsification. Optionally, the method further comprises removing the residual organic solvent. Optionally, the method further comprises removing the residual water solvent.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for making an oral dosage form selected from the group consisting of a candy, a chocolate, a cookie, a popsicle, a protein shake powder, a beverage, a beer, a soft drink, an alcoholic beverage, a gummy and a milkshake, the method consisting essentially of non-covalently binding a cannabinoid to a whey protein, consisting essentially of dissolving the cannabinoid in ethanol to form an ethanol solution; and then combining the ethanol solution with an aqueous whey protein to form a cannabinoid-protein complex which is then combined with at least one other excipient to form the dosage form, wherein the complex formed between the cannabinoid and the whey protein is performed using nanoprecipitation or emulsification.

2. The method according to claim 1, further comprising removing the residual ethanol before combining with the at least one other excipient.

3. The method according to claim 2, further comprising removing residual water before combining with the at least one other excipient.

4. The method according to claim 3, wherein the residual water is removed by freeze-drying or spray-drying to form a dried cannabinoid-protein complex.

5. The method according to claim 1, wherein the cannabinoid is tetrahydrocannabinol or cannabidiol.

6. The method according to claim 5, wherein the cannabinoid is tetrahydrocannabinol.

7. The method according to 18, wherein the cannabinoid-protein complex has a ratio of cannabinoid to protein of between 0.008 to 1 and 1.2 to 1.

8. The method according to claim 7, wherein the cannabinoid-protein complex has a ratio of cannabinoid to protein of between 0.025 to 1 and 0.5 to 1.

9. The method according to claim 1, wherein the whey protein is a water-suspended fraction of whey protein.

10. The method according to claim 1, wherein the oral dosage form is a gummy.

11. The method according to claim 10, wherein the at least one other excipient is selected from the group consisting of pectin and gelatin.

* * * * *